US012654164B2

(12) United States Patent
Van Workum et al.

(10) Patent No.: US 12,654,164 B2
(45) Date of Patent: Jun. 16, 2026

(54) SYSTEM COMPRISING AN APPARATUS AND A CARTRIDGE FOR ASSAY MEASUREMENT

(71) Applicant: Panacea Diagnostics Ltd, London (GB)

(72) Inventors: Stefan Leo Van Workum, London (GB); Vladimir Alexander Turek, London (GB); Marko Dorrestijn, London (GB); David R. Klug, London (GB)

(73) Assignee: Panacea Diagnostics Ltd, London (GB)

( * ) Notice: Subject to any disclaimer, the term of this patent is extended or adjusted under 35 U.S.C. 154(b) by 990 days.

(21) Appl. No.: 17/786,469

(22) PCT Filed: Dec. 18, 2020

(86) PCT No.: PCT/GB2020/053293
§ 371 (c)(1),
(2) Date: Jun. 16, 2022

(87) PCT Pub. No.: WO2021/123812
PCT Pub. Date: Jun. 24, 2021

(65) Prior Publication Data
US 2023/0021366 A1        Jan. 26, 2023

(30) Foreign Application Priority Data

Dec. 19, 2019     (GB) ...................................... 1918912

(51) Int. Cl.
*B01L 3/00*          (2006.01)
*G01N 21/64*        (2006.01)
*G01N 33/543*      (2006.01)

(52) U.S. Cl.
CPC .......... *B01L 3/5023* (2013.01); *G01N 21/648* (2013.01); *G01N 33/54388* (2021.08);
(Continued)

(58) Field of Classification Search
CPC ............. B01L 3/5023; B01L 2200/025; B01L 2200/04; B01L 2200/16; B01L 2300/022;
(Continued)

(56) References Cited

U.S. PATENT DOCUMENTS

| | | | |
|---|---|---|---|
| 10,307,754 B2 * | 6/2019 | Bau-Madsen .... | G01N 35/00029 |
| 2004/0101443 A1 * | 5/2004 | Kagan ................ | G01N 35/0098 |
| | | | 436/180 |

(Continued)

FOREIGN PATENT DOCUMENTS

| | | |
|---|---|---|
| EP | 2 997 372 B1 | 6/2019 |
| JP | 2011-237439 A | 11/2011 |

(Continued)

OTHER PUBLICATIONS

Combined Search and Examination Report under Sections 17 & 18(3) for GB Application No. 1918912.5 dated Jun. 10, 2020.
(Continued)

*Primary Examiner* — Samuel P Siefke
(74) *Attorney, Agent, or Firm* — Maine Cernota & Curran

(57)                    ABSTRACT

An apparatus (1) for detecting the presence and/or the quantity of a target component in a biological fluid in an integrated assay cartridge (52) of predetermined configuration, the assay cartridge comprising a capture component (22) at a predetermined location in the assay cartridge, the apparatus comprising: a detector (12) for detecting the amount of light scattered, transmitted or emitted by the sample to provide an indication of the presence and/or the quantity of the target component within the sample; three location positions (30), the three positions defining a loca-
(Continued)

tion along the optical path of the detector on which to locate the cartridge of a predetermined size; wherein location positions are configured such that the capture component of the assay cartridge is located, in use, at the focal plane of the detector. Measures to ensure quality control may also be provided.

17 Claims, 6 Drawing Sheets

(52) U.S. Cl.
CPC ..... *B01L 2200/025* (2013.01); *B01L 2200/04* (2013.01); *B01L 2200/16* (2013.01); *B01L 2300/022* (2013.01); *B01L 2300/0654* (2013.01)

(58) Field of Classification Search
CPC .......... B01L 2300/0654; G01N 21/648; G01N 33/54388; G01N 21/645; G01N 33/52
See application file for complete search history.

(56) References Cited

U.S. PATENT DOCUMENTS

| | | | |
|---|---|---|---|
| 2007/0166196 A1* | 7/2007 | Bardell | G01N 35/00663 |
| | | | 422/68.1 |
| 2008/0095669 A1 | 4/2008 | Kang et al. | |
| 2009/0154776 A1 | 6/2009 | Mott et al. | |
| 2012/0115214 A1* | 5/2012 | Battrell | G01N 21/645 |
| | | | 422/82.08 |
| 2016/0187333 A1 | 6/2016 | Moll et al. | |
| 2018/0246038 A1 | 8/2018 | Hunter | |
| 2018/0292319 A1 | 10/2018 | Battrell et al. | |
| 2022/0143597 A1 | 5/2022 | Dorrestijn et al. | |
| 2022/0143608 A1 | 5/2022 | Van Workum et al. | |
| 2022/0146425 A1 | 5/2022 | Van Workum et al. | |
| 2022/0146505 A1 | 5/2022 | Dorrestijn et al. | |

FOREIGN PATENT DOCUMENTS

| | | | |
|---|---|---|---|
| WO | 02/08762 A1 | 1/2002 | |
| WO | 2005/111617 A1 | 11/2005 | |

OTHER PUBLICATIONS

Invitation to Pay Additional Fees for International Application No. PCT/GB2020/053293 dated Apr. 7, 2021.
International Search Report and Written Opinion for International Application No. PCT/GB2020/053293 dated May 31, 2021.
International Preliminary Report on Patentability for International Application No. PCT/GB2020/053293 dated Jun. 30, 2022.
U.S. Appl. No. 14/435,372, filed Aug. 31, 2021, Van Workum et al.
U.S. Appl. No. 17/435,373, filed Aug. 31, 2021, Van Workum et al.
U.S. Appl. No. 17/435,375, filed Aug. 31, 2021, Dorrestijn et al.
U.S. Appl. No. 17/435,376, filed Aug. 31, 2021, Dorrestijn et al.
U.S. Appl. No. 17/786,435, filed Jun. 16, 2022, Van Workum et al.
U.S. Appl. No. 17/786,440, filed Jun. 16, 2022, Van Workum et al.
GB 1918912.5, Jun. 10, 2020, Combined Search and Examination Report under Sections 17 & 18(3).
PCT/GB2020/053293, Apr. 7, 2021, Invitation to Pay Additional Fees.
PCT/GB2020/053293, May 31, 2021, International Search Report and Written Opinion.
PCT/GB2020/053293, Jun. 30, 2022, International Preliminary Report on Patentability.

* cited by examiner

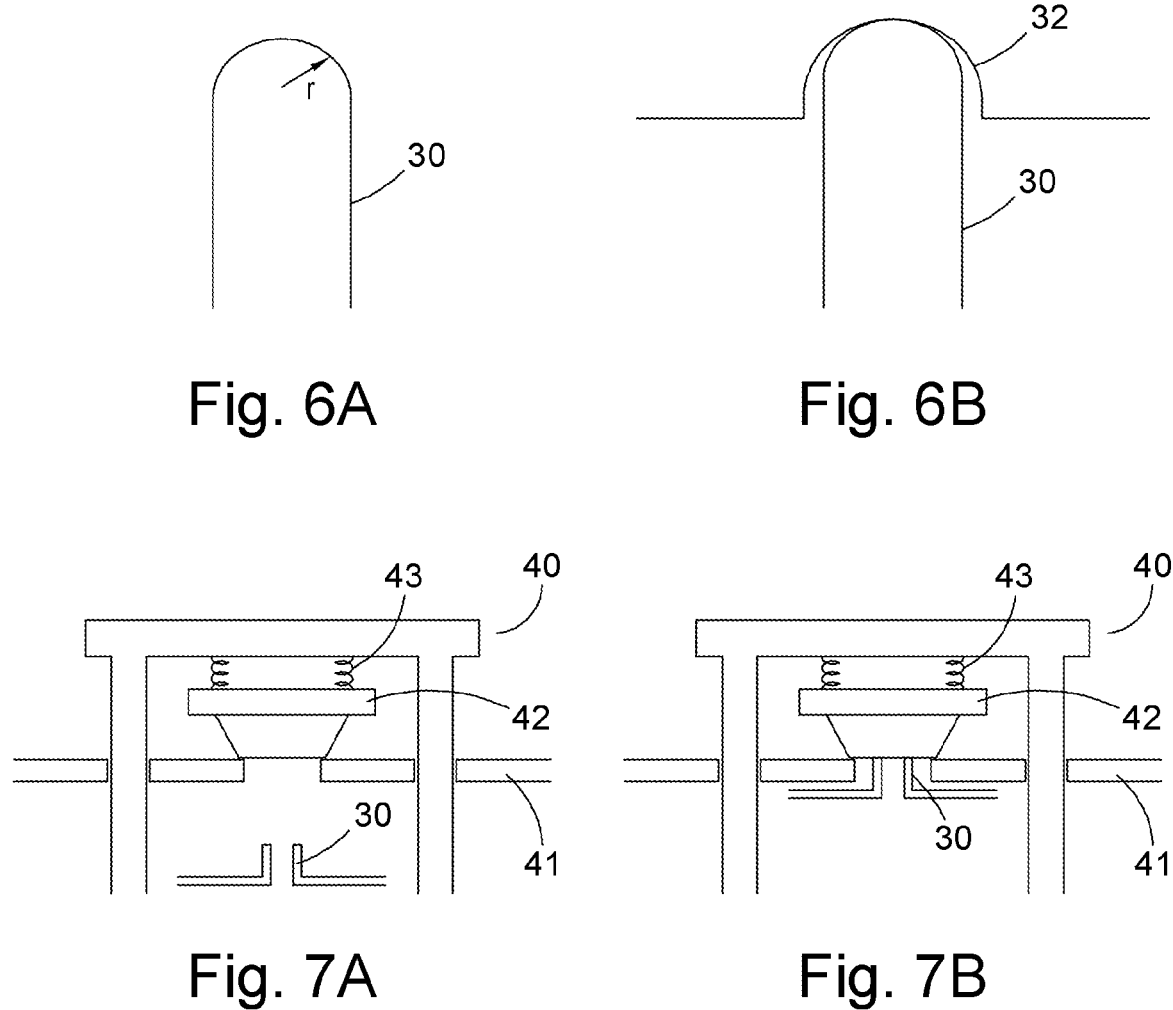
Fig. 6A          Fig. 6B
Fig. 7A          Fig. 7B
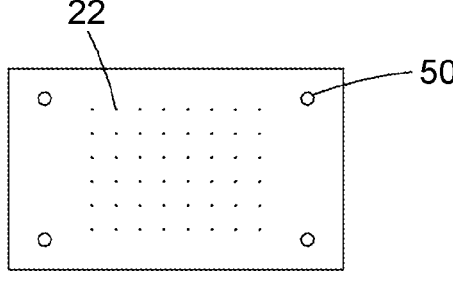
Fig. 8

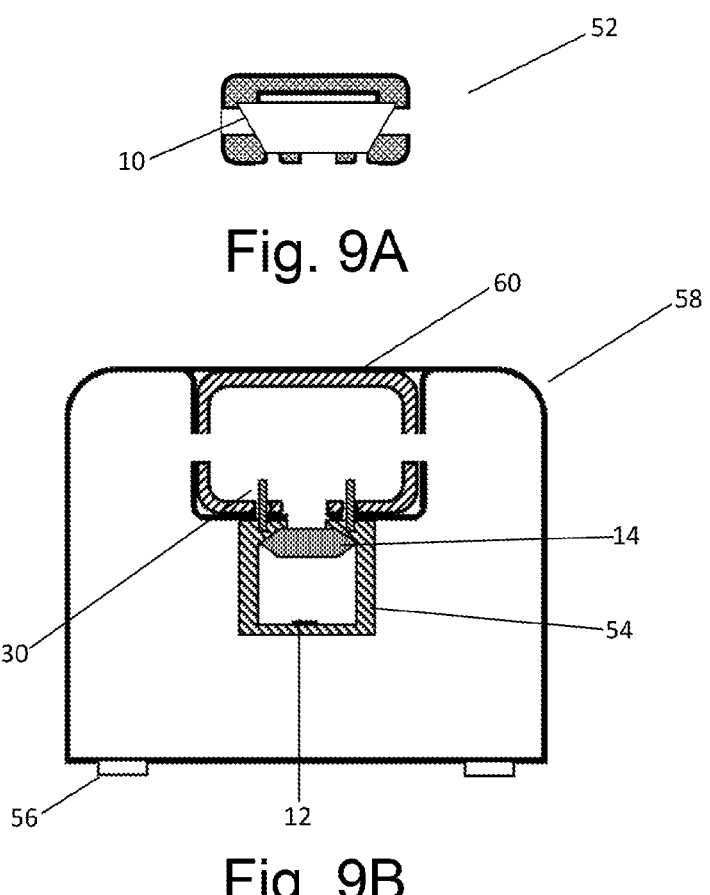
Fig. 9A
Fig. 9B
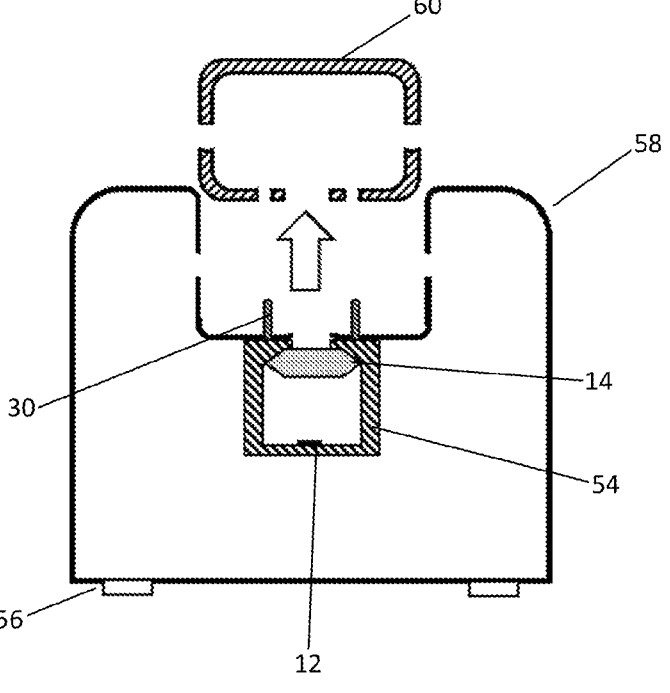
Fig. 9C

SYSTEM COMPRISING AN APPARATUS AND A CARTRIDGE FOR ASSAY MEASUREMENT

RELATED APPLICATIONS

This Application is a national stage filing under 35 U.S.C. § 371 of International Patent Application Serial No. PCT/GB2020/053293, filed Dec. 18, 2020, entitled "SYSTEM COMPRISING AN APPARATUS AND A CARTRIDGE FOR ASSAY MEASUREMENT," which claims priority to GB application number GB 1918912.5, filed Dec. 19, 2019, each of which is herein incorporated by reference in their entireties.

The present invention relates to improvements in the measurement of biomarkers in a sample in a cartridge.

A self-contained diagnostic system often includes a disposable cartridge and a detector/reader. The cartridge can be inserted into the detector and the sample such as a blood, saliva or urine can be analysed. Bioassays are often performed on a device such as an assay cartridge in order to detect certain biomarkers within a sample which is within the cartridge. Integrated assays include all reagents necessary for the assay within the cartridge and can therefore be used by unskilled operators in domestic settings, in contrast to conventional arrangements in which medical professionals may add reagents to the assay.

In this context, the term domestic setting or application is intended to encompass any non-clinical environment such as the home, workplace, pharmacy or doctor's surgery. A domestic application can also be a high throughput application, for example the daily testing of employees in the workplace to identify pre-symptomatic flu, which requires a high volume of cartridges to be assayed in a short timeframe.

In an integrated assay, a user supplies a sample into the assay cartridge which comprises all reagents necessary for the assay within the cartridge including a detection reagent with an attached label. The detection reagent is specific to the target component to be detected and will bind to the target component if present in a sample. At a given location within the cartridge are capture components to which the target component and detection reagent with attached label will bind.

The detection reagent binds to the target component to form a detection reagent-target component complex. This complex then binds to the capture component to form a sandwich assay. The detection reagent can have inherent light emitting or scattering properties or the detection reagent may have applied to it a label. The detection reagent may be an antibody or an antibody fragment, protein or a peptide, or a nucleic acid.

The label may be one or more of the following: a luminescent entity; a fluorescent entity; a phosphorescent entity; a chemiluminescent entity; an entity that exhibits scattering, such as Rayleigh, Raman or Mie scattering; an entity that exhibits photon upconversion; an enzyme and its substrate that together produce an optical signal such as a luminescent signal and any entity providing a colorimetric signal regardless as to process but specifically exemplified by change to absorption cross section or extinction. In this context, the term upconversion is used to denote any emission following a multi-photon excitation process and this includes two photon fluorescence particles.

In this context, the term entity is used to refer to one or more of the following: a molecule; a cell or cell fragment such as a fragment of cell membrane; an ion; a particle which may be metallic, organic, inorganic or polymeric; a nanoparticle; a cluster, or a quantum dot.

To obtain a quantitative result the sample is illuminated resulting in luminescence and/or scattering which can be detected. However, if the sample is incorrectly illuminated there will be unpredictable luminescence and/or scattering.

With the sample illuminated an optical measurement is taken. However, the amount of light collected may vary which can result in an unreliable signal and decreases the accuracy of the resulting measurement.

Furthermore, it is important for quality control that each sample is consistently illuminated and that the amount of light collected from reference spots is consistent between samples and that any inconsistencies in the illumination can be detected and if within allowable limits adjusted for. The intensity of the light captured from the capture component location and therefore the bound detection reagent may vary from sample to sample.

Tests involving precise measurements and precise alignment are conventionally carried out by trained professionals. Although integrated assays can be used by unskilled operators it is desirable that an unskilled operator should be able to obtain a quantitative result from the integrated assay.

Precise alignment can be facilitated by an optical autofocus mechanism. However, this can hinder the accurate measurement of luminescence, increase the complexity of the reader, and/or the time required for each assay.

JP2011237439A discloses a sample detection apparatus and a sample analysis apparatus that do not require an optical autofocus operation. This device has a means for performing a tilt operation for focusing on a substrate by moving 3 points (rods) outside an area for detecting a sample on a substrate along a tilt direction. Each rod can be moved individually. A focusing operation can be performed by adjusting the relative positions of the objective lens and the substrate in accordance with information on the substrate (e.g., the thickness of the substrate, the refractive index of the material of the substrate, and the amount of movement of the rod) determined in advance. The drive system of the rod includes a drive motor provided at or near the cartridge installation portion. In order to accurately position the rod, the drive motor is connected to a drive motor control. A gear is also provided and the driving force of the drive motor is transmitted to the rod via the gear. The drive motor and the gear exist independently from each of the 3 rods, allowing the biochemical reaction cartridge (substrate) to be tilted and moved along the optical axis.

Therefore the disclosed device comprises several moving parts, which move or tilt a substrate along an optical axis to enable a focusing operation. The moving parts add complexity and expense to the device and decrease the durability and suitability for the device to be used in a high-throughput application.

There is a need to provide an alignment solution that allows consistent illumination of samples for quantitative luminescence and/or scattering readings, and is suitable for use by an unskilled user in a setting such as a domestic setting. An alignment solution is required that is robust and durable without adding considerable cost and complexity to the diagnostic system so that it is compatible for repeated use within the home, workplace or retail environments which are the target for this innovation.

It is against this background that the present invention has arisen.

According to the invention there is provided an apparatus for detecting the presence and/or the quantity of a target component in a biological fluid in an integrated assay cartridge of predetermined configuration, the assay cartridge comprising a capture component at a predetermined location in the assay cartridge, the apparatus comprising a detector for detecting the amount of scattered, transmitted or emitted light to provide an indication of the presence and/or the quantity of the target component within the sample, three location positions, the three positions defining a location along the optical path of the detector on which to locate the cartridge of a predetermined size; and wherein location positions are configured such that the capture component of the assay cartridge is located, in use, at the focal plane of the detector.

The use of location positions allows the cartridge to be accurately positioned and thus the capture components (located at a known location with the cartridge) accurately illuminated and a reliable signal and measurement taken from the sample. This obviates the need for costly and complex movement of the optics relative to the sample. Additionally, because each and every sample is consistently illuminated and measured inconsistencies between samples are reduced. Thus this apparatus provides a self-contained, quantitative diagnostic system which can be used by an unskilled operator.

The detector and the three location positions are fixed in position. The location positions guide the cartridge into the correct position in the x and y directions, and the capture component, at a predetermined location in the assay cartridge, is aligned as accurately as possible along the z dimension. The accurate alignment along the z dimension is facilitated by a precise control of substrate thickness and capture component location within the cartridge, maintaining the cleanliness of all device components, minimising thermal drift, and avoiding any relative motion within the apparatus. The alignment of the cartridge is passive and does not require movement of the detector or precise manipulation of the cartridge, the optical detector, or the imaging system by the user. The reduced complexity of the apparatus results in a robust and durable diagnostic system which is ideal for use in a high-throughput application. The assay cartridge is an integrated assay cartridge which includes all the reagents necessary for the assay. As no exogenous products are needed the assay can be run by an unskilled operator, for example, in a domestic setting. The present invention provides a method in which an unskilled user can use the integrated assay to obtain a quantitative result.

Illuminating the capture component excites the label attached to the detection reagent and it is this which emits, scatters or transmits light.

In some embodiments each of the three location positions are positioned away from the optical path of the detector. This reduces the tendency of the assay cartridge to rock or roll and ensures most stability for the optical element. The stability of the assay cartridge and optical element facilitates an accurate alignment of the capture component, at a predetermined location in the assay cartridge, along the optical path. The location positions may be in plane perpendicular to the optical axis of the apparatus.

The apparatus may comprise a location plate on which the location positions are positioned. Alternatively only one or two of the location positions may be located on the location plate. A location plate is a convenient way of providing the location positions. If the location plate is within the optical path in may include a hole.

Each of the three location positions may be equidistant from the central optical path of the detector which means that each of the three location positions is equally significant and inaccuracies in one would not dominate the others.

The location positions may be arranged on location pins, each location pin having a distal end on which to locate the cartridge, the distal ends of the pins having a domed tip. Location pins are a convenient configuration and the provision of a single point of contact on a domed tip gives greater positional accuracy than a flat surface.

The location pins may be stainless and corrosion protected to prevent a change in the position of the distal tip of the location pins due to, for example, a build-up of rust. Stainless and corrosion protected location pins ensure the apparatus is durable and suitable for repeated use in a high-throughput application.

There may be an excitation light source configured to excite a detection reagent attached to the target component. The excitation light source provides an incident light beam which is configured to generate an evanescent excitation field in the form of total internal reflection (TIR) at the substrate upon which the detection reagents are located.

There may be further provided a means for biasing the assay cartridge onto the location positions which ensures that the assay cartridge remains firmly in place. The means for mechanically biasing the assay cartridge onto the location positions may comprise at least one of: mechanical biasing means; pneumatic biasing means; hydraulic biasing means; piezoelectric means an inflatable pad; heat actuated material. As an example a pin may be biased against the assay cartridge. In another example, the biasing means may be a spring which forms part of a lid. When the user applies force to close the lid, the assay cartridge is biased onto the location positions without requiring further input from the user. Alternatively, or additionally other indirect (non-contact) biasing means such as electromagnetic biasing means; magnetic biasing means could also bias the chip onto the location positions The assay cartridge may be loaded onto the location positions along the optical path. The optical axis, or z direction, is most critical for alignment and by loading the cartridge along this axis better alignment along the most critical direction is achieved. It is the final step of loading the cartridge which is preferably along the optical axis. Prior to the final step the cartridge may be loaded at other orientation or by for example, a carousel.

There may be further provided an indicator configured to detect the presence of a cartridge. The indicator may comprise an electrical connection with the cartridge and it may be possible to identify the individual cartridge this way. As another alternative the indicator may use RFID. Other alternatives include a barcode or QR code scanner.

Reference spots comprise spots which scatter, transmit or reflect light and they may be formed as part of the optical element, for example a dimple or dome or a reflective portion or alternatively may be formed by a substance on the surface of the optical element. Alternatively or additionally, capture components may be arranged on the optical element in the form of an array of dots. One or more capture component dots may be a reference spot. There may be reference spots on the cartridge which can be used as a quality control check. Alternatively or additionally, the reference spot can be any mark, either scratched into or embossed onto the optical surface, or any other form of scribed marking on the cartridge. The quality control may confirm both the location of the cartridge and also characteristics of the illumination beam and the configuration of the apparatus.

There may be a reference checker to detect and check the location of a reference spot in the cartridge. This enables the position in a plane perpendicular to the optical path to be checked.

The reference checker may check the focus of the reference spot. This helps to check the position of the reference spot, and thus the cartridge along the optical path. Alternatively or additionally, the reference checker may compare an image of the reference spot to a stored image to determine alignment accuracy.

Multiple reference spots may be used and the use of multiple spots can be used to check the beam shape and therefore the reference checker can be configured to check the position of a plurality of reference spots.

Additionally or alternatively, the reference checker can determine the intensity of the one or more reference spots. This can determine how well the chips is aligned to the excitation beam, how the power of the excitation beam is distributed across the field of view and also how well the cartridge is aligned in the z direction.

Alternatively or additionally, the reference checker may determine the intensity profile of light scattered, transmitted or emitted by the one or more reference spots.

The reference checker may check the location, focus or intensity of one or more reference spots, and determine the reference spot is not consistent with a stored threshold, image or value. The reference checker may provide an indication to the user and prevent any further measurements being taken until the apparatus has undergone maintenance. If the reference checker does not detect any reference spots, then the reference checker provides an indication to the user. This is a quality control feature which prevents inaccurate measurements as a result of misalignment in the apparatus.

The target component may be a specific peptide or protein or nucleic acid or small molecule. The target components may be a specific combination of peptides, proteins, nucleic acids or small molecules determined by the characteristics to be investigated.

The sample may be a saliva sample. Providing a saliva sample is a simple, non-intrusive procedure. As a result, users are typically more willing to provide a saliva sample than, for example, a blood sample. Furthermore, this increases the frequency with which a user can be expected to provide a sample. By providing frequent samples, a personalised base line can be established for each user allowing a personal profile to be established and therefore feedback can be provided if level fall outside the expected levels for that individual. These can be a much tighter set of parameters than for the population as a whole.

The use of saliva as the sample fluid is also appropriate to a wider range of settings, for example the home or even the workplace. In some embodiments, all employees may be requested to provide a daily sample in order to look for pre-symptomatic flu. This can enable an employee to be sent home before symptoms develop, potentially reducing the number of colleagues infected by that individual and also potentially lessening the symptoms of the infected individual as a result of taking time off in advance of symptoms presenting.

The sample may form part of a lateral, or free flow assay. The method can be used to make a quantitative assessment of the amount of a target component in a lateral flow assay.

According to the invention there is a method for detecting the presence and/or the quantity of a target component in a biological fluid in an assay cartridge of predetermined configuration, the assay cartridge comprising a capture component at a predetermined location in the assay cartridge, the method comprising: positioning the cartridge on three location positions, the three positions defining a location along the optical path of the detector in which to locate the cartridge of a predetermined size; illuminating the capture component; detecting the amount of light scattered, transmitted or emitted by the label encapsulated within the detection reagent to provide an indication of the presence and/or the quantity of the target component within the sample; wherein location positions are configured such that the capture component of the assay cartridge is located, in use, at the focal plane of the detector.

According to the invention there is provided a method for detecting the presence and/or the quantity of a target component in a biological fluid in an integrated assay cartridge of predetermined configuration, the integrated assay cartridge comprising a reference spot and a capture component at a predetermined location in the assay cartridge, the method comprising: positioning the cartridge on three location positions, the three positions defining a location along the optical path of the detector in which to locate the cartridge of a predetermined size, the location positions being configured such that the capture component of the assay cartridge are located, in use, at the focal plane of the detector; illuminating the capture component and reference spot; detecting the amount of light scattered, transmitted or emitted by reference spot; determining the focus based on the reference spot; determining the intensity of light scattered, transmitted or emitted by the sample from the area of the capture component to determine a spot intensity; and determining a calibrated spot intensity based on the focus of the reference spot.

The accuracy of focus can be found using the reference spot. If the sample is out of focus the amount of light collected from the sample will vary. If the deviation from accurate focus is known then an adjustment can be made to account for the amount of light not collected due to deviation from accurate focus. Additionally or alternatively, the reference checker may provide an indication to the user that there is a deviation from accurate focus and prevent any further measurements being taken until the apparatus has undergone maintenance.

According to the invention there is provided a method for detecting the presence and/or the quantity of a target component in a biological fluid in an integrated assay cartridge of predetermined configuration, the integrated assay cartridge comprising a reference spot and a capture component, the capture component being at a predetermined location in the assay cartridge, the method comprising: positioning the cartridge on three location positions, the three positions defining a location along the optical path of the detector in which to locate the cartridge of a predetermined size, the location positions being configured such that the capture component of the assay cartridge are located, in use, at the focal plane of the detector; illuminating the reference spot and capture component; determining the location of the reference spot; detecting the expected boundary of the capture component; detecting the amount of light scattered, transmitted or emitted by the sample within the boundary of the capture component to determine a spot intensity.

The amount of light scattered, transmitted or emitted from an area outside the boundary of the capture component may also be detected and moderated spot intensity calculated based on the spot intensity and the amount of light scattered, transmitted or emitted from an area outside the boundary of the capture component.

Detecting the boundaries of capture components is important because this allows the signal to be distinguished over the background signal from the area outside the capture component boundary. The boundaries of the capture components can be determined using the position of the reference spots.

A further advantage of accurate detection of spot location is that smaller spot sizes can be used as it is possible to accurately distinguish between the signal from the capture component area and other areas. This allows for more capture component spots within a given area.

The invention will now be further and more particularly described, by way of example only, and with reference to the accompanying drawings, in which:

FIGS. 6A and 6B depict details of the location pins;

FIG. 7A depicts an optical element positioned in the apparatus prior to loading onto the location plate;

FIG. 7B depicts the apparatus of FIG. 7A with the optical element being loaded onto the location plate; and FIG. 8 depicts an array of spots on the optical element.

FIG. 9A depicts an assay cartridge;

FIG. 9B shows the detection apparatus within a light-tight case;

FIG. 9C shows the light-tight case in an open position; and

Figure 1:
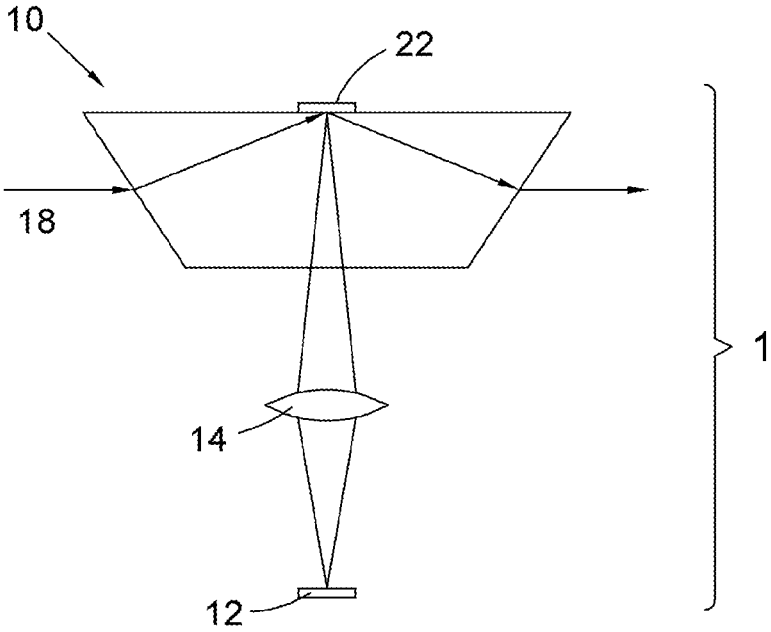
FIG. 1 shows, schematically, the detection apparatus.

Referring to FIG. 1, there is provided an apparatus 1 for detecting the presence and/or the amount of a target component in a biological fluid. An incident light beam 18 enters an optical element an illuminates capture components 22. The apparatus comprises an assay cartridge including an optical element 10 and a detector 12 for detecting the presence and/or the amount of the emitted light to provide an indication of the presence and/or the amount of the target component within the sample. In addition, there is provided an imaging lens 14, which may be located between the optical element 10 and the detector 12. In some instances, one or more imaging lens may be provided and the term "lens" is intended to cover optical elements or optical systems, including relay optics. The imaging lens 14 can be used to focus the emitted light from the detection reagents, attached to the target components, onto the detector 12, as shown in FIG. 1. Although not depicted FIG. 1 may include other optical elements such as relay optics.

FIG. 1 depicts a capture component 22 illuminated using total internal reflection fluorescence. However, the component could also be illuminated either directly from above or directly from below. Alternatively, the capture component may be illuminated at an oblique angle and dark field imaging used in the detection.

The detection reagent binds to the target component to form a detection reagent-target component complex. This complex then binds to the capture component to form a sandwich assay. The detection reagent can have inherent light emitting or scattering properties or the detection reagent may have applied to it a label. The detection reagent may be an antibody or an antibody fragment, protein or a peptide, or a nucleic acid.

The label may be one or more of the following: a luminescent entity; a fluorescent entity; a phosphorescent entity; a chemiluminescent entity; an entity that exhibits scattering, such as Rayleigh, Raman or Mie scattering; an entity that exhibits photon upconversion; an enzyme and its substrate that together produce an optical signal such as a luminescent signal and any entity providing a colorimetric signal regardless as to process but specifically exemplified by change to absorption cross section or extinction. In this context, the term upconversion is used to denote any emission following a multi-photon excitation process and this includes two photon fluorescence particles.

In this context, the term entity is used to refer to one or more of the following: a molecule; a cell or cell fragment such as a fragment of cell membrane; an ion; a particle which may be metallic, organic, inorganic or polymeric; a nanoparticle; a cluster, or a quantum dot.

Although the term "emitted light" is used it may be the emitted light, the scattered light, the transmitted light, or the absorbed light which is detected and analysed. Detected components may include a variety of peptides and/or proteins.

Figure 2:
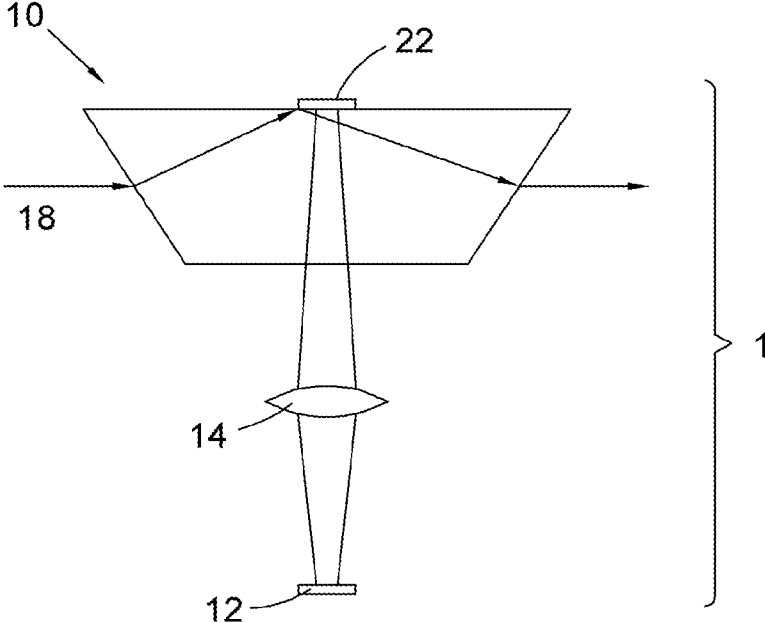
FIG. 2 shows, schematically, the detection apparatus with an incorrectly illuminated and out of focus sample and detection reagent.

FIG. 2 depicts an alternative in which the optical element 10 is not correctly located. Thus the incident light beam does not adequately illuminate the capture components 22 and thus bound sample with detection reagent and the emitted light is not accurately focused on the detector and this reduces the accuracy of the detection.

In order to ensure that the capture component is accurately illuminated a plurality of location pins 30 may be provided on a location plate 29. If placed directly in the optical path the location plate has a hole in the centre to allow the light to pass through. The optical element 10 is generally of standard, known dimensions, with the capture components arranged at a known location on the optical element. The location pins 30 are positioned such that when an optical element of known dimensions is positioned on the location pins the upper surface 21 of the optical element 10 is in the focal plane of the detector and is positioned to be illuminated by the incident light beam. The location pins are rigidly held in position although, as discussed below, the position can be adjusted to allow for optical elements 10 of different configurations and dimensions. Critically, the location pins are configured such that the capture components are within the focal plane of the detector.

As depicted in FIG. 3 the distal ends 31 of the location pins may be domed so that each location pin has a known, single point of contact with the optical element 10. Additionally, the location pins 30 may be made of a corrosion resistant material such as stainless steel which prevents the location of the distal end of the location pins from changing over time due to the build up of rust. The corrosion resistant material may be stainless steel or aluminium and could be coated or treated to improve durability. Optical elements 10 may be made of glass or plastic and the optimal choice of both the material and configuration/shape of the location positions, or pins, may depend on the material of the optical element.

If the location pins are formed of electrically conductive material they may be used to carry an electrical current used to detect the presence of the cartridge via a detection of conductive material or coating that forms part of the cartridge. If three location pins are used a conductivity threshold may be used to verify contact. For example, the conductivity, and connection through each pin could be verified to ensure that all three location pins are connected. Additionally this could be used to detect the ID of the chip.

Alternative methods of detecting the ID of the chip such as bar codes, RFID may also be used and the apparatus may include devices for use with these methods.

Figures 3A, 3B:
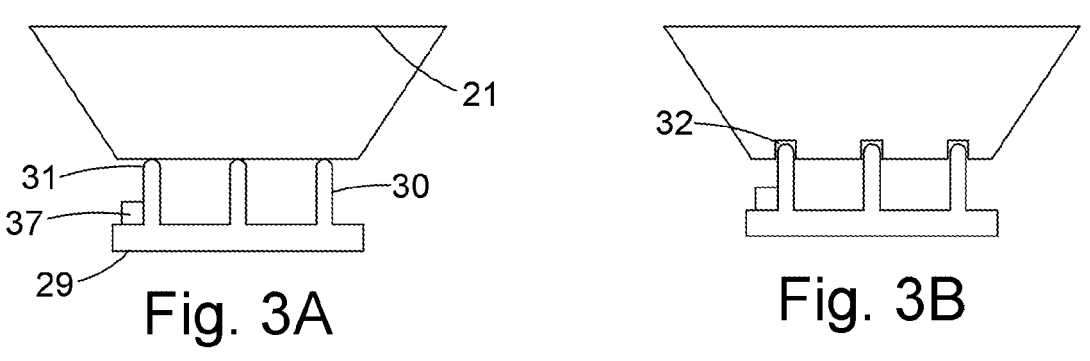
FIGS. 3A, 3B, 3C and 3D depict, schematically, an optical element supported by a location plate.

As an alternative to using electrical conductivity to verify the presence of a cartridge a capacitance test could be used to check the contact area. All but one of the pins may be coated in a dielectric such as a polymer or silicate. The other pin is not coated in the dielectric and is used to measure capacitance across the other pins. FIG. 3B depicts an alternative embodiment in which the location pins 32 are positioned in recesses within the optical element 10. Again, the location pins are arranged such that the upper surface of the optical element is in the focal plane of the detector.

It will be understood that, in this context "upper" refers merely to the illustrated configuration as displayed on the accompanying drawings, it should not be construed to limit the use of the optical element to this configuration. In use, the optical element may be held in any orientation without limitation.

FIGS. 3A and 3B each depict three location pins and these are positioned away from the optical path, or optical axis of the apparatus. The may be arranged equidistant from the optical path or different distances from the optical path. As depicted in FIGS. 3A and 3B the distal ends of the location pins 10 are within a plane perpendicular to the optical path, although different arrangements with, for example, the distal ends could form a plane which is not perpendicular to the optical axis.

Although FIGS. 3A and 3B depict three location pins 30 defining three location positions to support the optical element 10 there may be more location pins as necessary for the apparatus. A greater number of points of contact, or pins may generate less accurate positional accuracy due to them interfering with each other but also carries a benefit of reducing the optical element 10 rocking. Thus the number of pins must be carefully chosen and statistics can be used to select the appropriate number of points of contact.

Figure 3C:
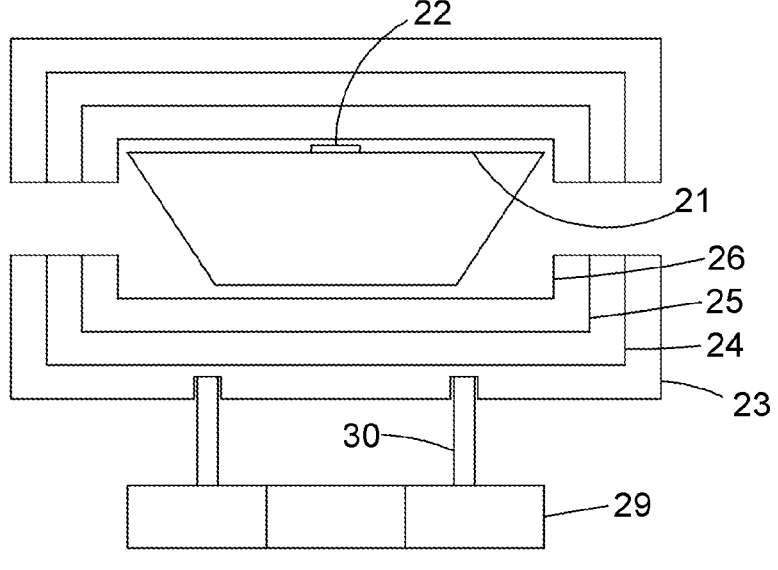

FIG. 3C depicts an arrangement in which optical element is located on additional layer 26, which is on additional layer 25, which is on additional layer 24, which is on additional layer 23 which is located on the location pins. Additional layers may be used in the construction of the cartridge but the capture component of the assay cartridge must be located, in use, at the focal plane of the detector. Thus, if additional layers are used the position of the location positions, or location pins may need to be adjusted and the achievable reproducibility of the positioning system may decrease with each additional layer.

Figure 3D:
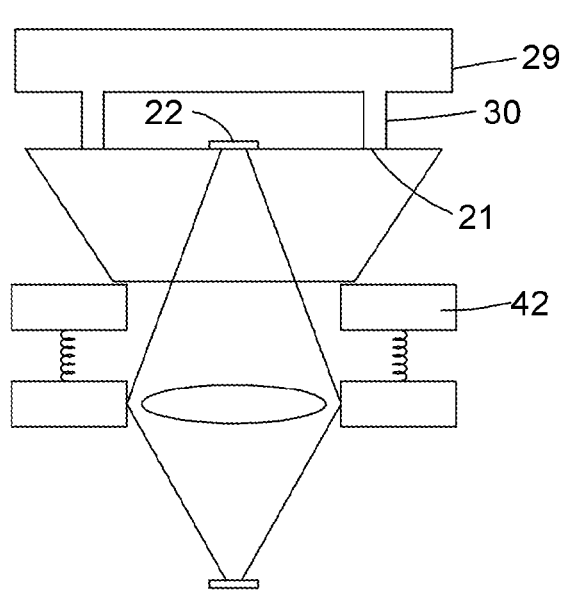
Figure 4:
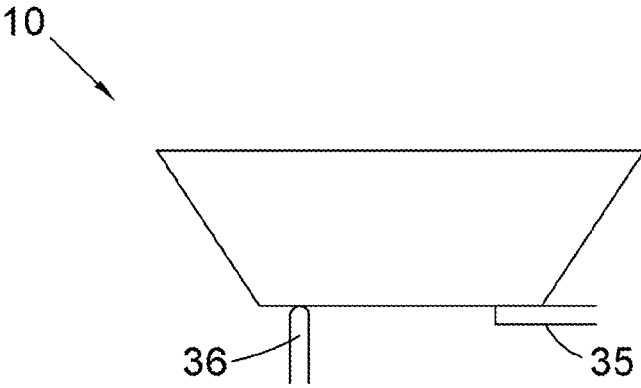
FIG. 4 depicts an alternative arrangement to support the optical element.

FIG. 3D depicts an alternative arrangement in which the optical element 10 is positioned on some location pins above, rather than below (as depicted in FIGS. 3A, B and C). This has the advantage that the apparatus can be used with different sizes of optical elements rather than with an optical element of known dimensions. FIG. 4 depicts an alternative in which optical element 10 is positioned on a support surface 35 and a location pin 36. In this embodiment the support surface forms two location positions with the location pin 36 providing a third location position.

Figure 5:
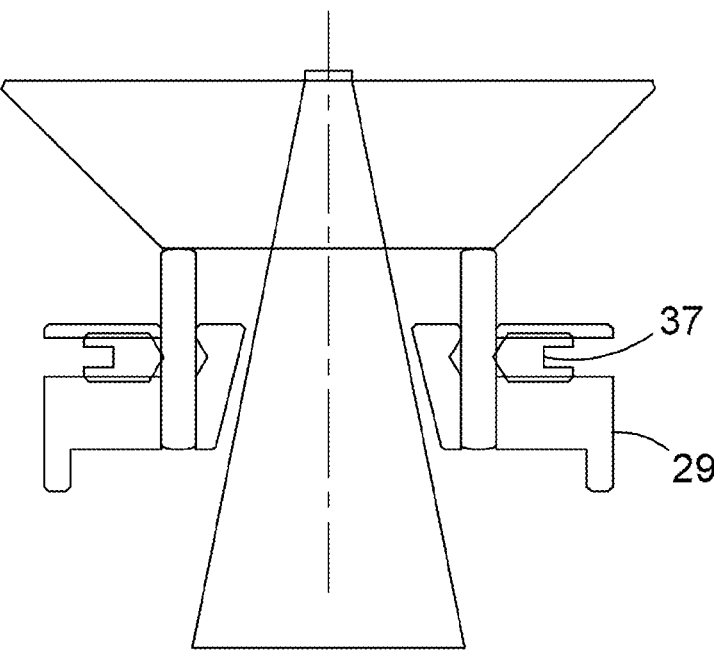
FIG. 5 shows a detail of the location plate.

FIG. 5 shows the location plate of FIGS. 3A and 3B in more detail. In this view, only two location pins are depicted while the third is out of view. The embodiment depicted herein allows the apparatus to be adapted for use with optical elements of different dimensions, in particular by allowing the height of the location pins 30 to be adjusted. Set screws 37 are used to fix the height of the location pins with respect to the location plate 29 and the height can be adjusted during a calibration process, for example, in a factory setting. With the set screws loosened the location pins may be free to move, or alternative the height may be adjusted by a screw mechanism (not depicted). Thus to adjust the height of the location pins the set screws 37 can be loosened, the height of the location pins adjusted either by free movement or via a screw mechanism, and the set screws are then tightened to securely fix the height of the location pins. As an alternative to set screws a clamp may be used or the pins may be threaded to move vertically to the desired position when rotated. Another alternative is the use of a piezoelectric actuator to adjust the height of the location pins. Although this would not generally be adjustable by the user it could by adjusted by the manufacturer in response to a system modification.

FIG. 6A depicts a location pin with a curved tip. As can be seen the tip is domed which gives a small, and thus accurate, accurate contact point. Similarly, the tip may be curved, conical or have a chamfer. Preferably the tip of the location pin has a radius such that there is a small contact point.

FIG. 6B depicts the tip of a location pin. As can be seen, the counter surface to the domed tip has a corresponding shape to the tip of the location pin instead of being flat, as depicted in earlier Figures.

As depicted in FIGS. 3B and 6B the location pins can be positioned in recesses 32. If recesses are used then locations pins with decreasing radii at their tips also aid location of the optical element in the plane perpendicular to the optical path (in the x and y directions). As the optical element 10 is loaded onto the location pins it is guided into the correct position in the x and y directions.

The optical element 10 is preferably loaded onto the location pins along the optical axis which ensures that the most critical dimension, the z dimension, is aligned as accurately as possible. If aligned correctly with a gravitational field the weight of the optical element itself may be sufficient to position the optical element on the location pins but FIG. 7A depicts an apparatus for doing so. The optical element 10 is positioned onto a cradle 41. The cradle 41 forms part of a lid 40, also comprising a plate 42 and biasing means 43. In the present embodiment the biasing means are springs, but the biasing means may be any one, or combination of mechanical biasing means, electromagnetic biasing means, magnetic biasing means, an inflatable pad, pneumatic biasing means, hydraulic biasing means, heat actuated material or piezoelectric means.

FIG. 7B depicts the lid in a "closed" position with the optical element 10 positioned on the location pins 30. The biasing means 43 ensures that the optical element 10 is forced into firm contact with the location pins and the plate 42 ensures that the force is distributed across the entire of the optical element 10. Additionally a pin (or pins) could be used to provide the biasing The present invention may be used in conjunction with lateral flow assays in which the sample is formed by a lateral flow assay. Components captured in a lateral flow assay can be detected using the detection methods described above. For example, a target component can bind to an antibody with an attached label which is then bound to capture components. The sample can then be illuminated to determine the quantity of target components. Although lateral flow assays are conventionally assessed simply to determine whether or not a target component is present the present method provides a way of assessing quantitatively how much of a target component is present.

FIG. 8 depicts capture components arranged on the optical element. As can be seen the capture components may take the form of an array of dots 22. According to the specific configuration a single spot may be within the field of view of the detector or multiple spots.

The light scattered, transmitted or emitted by labels encapsulated with detection reagents in within the capture component area is detected. The light scattered, transmitted or emitted from areas outside the capture component area can also be detected and this can be used to calculate a moderated spot intensity. For example, the intensity of light from areas outside the capture component area can be subtracted from the intensity of light from areas within the capture component area.

There are, additionally, one or more reference spots 50 which can be used for quality control purposes to check that the optical element is correctly aligned. Reference spots comprise spots which scatter, transmit or reflect light and they may be formed as part of the optical element, for example a dimple or dome or a reflective portion. Alternatively they may be formed by a substance on the surface of the optical element. The apparatus comprises a reference checker and features of the reference spot can be determined and compared to reference values. Additionally, or alternatively, the reference checker may compare images of the reference spot(s) to reference images taken during machine manufacture or calibration or to images of the cartridge during manufacture that is linked via the cartridge ID. Images, or data related to the reference spot(s) may be detected and the data and/or images transmitted and processed remotely.

The reference spots may be used in many aspects of quality control. The x and y positions of a reference spot 50 can be compared to a stored, known pixel, location or compared to a reference image to determine alignment in the x and y direction and if there is more than one reference spot the rotational position of the optical element can be detected. Using this data it is possible to check the location of the cartridge with respect to the position of the detector and lens to ensure that the capture components are within the field of view and their locations within the field of view can be determined to aid in analysis of the signal from the detection region attached to the capture component. If the reference spot is determined to be out of alignment, then an indication is provided to the user and further measurements are prevented from being taken until the apparatus has undergone maintenance. This indication may take the form of a direct, visual communication to the operative. Alternatively, or additionally, it may take the form of communication via on board telemetry to the service provider. This communication may take the form of a warning associated with any subsequently provided data that the data should be treated as having a lower level of accuracy than would usually be expected. This communication may also be pushed to maintenance scheduling so that a call out can be provided to rectify the fault with the reader. As the capture components are in a known location relative to the reference spot, once the position of the reference spot is accurately known the position(s) of the capture components are also known. Thus the boundaries of the capture components are known so the signal from the capture component area can be accurately ascertained. Furthermore, the signal from the area outside the capture component area obtained i.e. the signals from within and outside a capture component area can be accurately distinguished. These can be used to determine a moderated spot intensity, as described above.

The size of a reference spot on the detector can be detected in order to detect whether the reference spot is in focus. The detected size can be compared to a reference size and used to determine the accuracy of the alignment along the z axis and, if there is more than one reference spot any angular deviation in the optical element may be detected. The intensity distribution of the image of a reference spot on the detector can also be analysed and used to determine accuracy in the z direction.

The reference spots may also be used in other ways. The intensity of light, sometimes measured as the signal/background noise ratio can be used to analyse how the excitation source illuminates across the field of view or how well the capture components 22 are aligned to the excitation source.

The accuracy of focus of the reference spot indicates the accuracy of focus for the sample as a whole. Thus if the accuracy of focus of the reference spot is known then this can be used to calculate a calibrated spot intensity to account for the variation in the light detected due to the lack of focus.

Referring to FIGS. 9A to 9D, an example is illustrated in which the detection apparatus is housed in a light-tight case 58. An assay cartridge 52 can be inserted into and removed from the light-tight case 58 as required. The light-tight case 58 prevents any excitation light from leaving the enclosure, which protects the user, and also prevents light from the environment interfering with measurements.

FIG. 9A shows an integrated assay cartridge 52 before insertion into the light-tight case 58. The assay cartridge 52 includes an optical element 10.

Referring to FIG. 9B, the light-tight case 58 includes an outer enclosure 60, which can accommodate an assay cartridge 52. The light-tight case 58 also comprises an imaging lens 14, location pins 30 (only two are shown, although three will be present) and a detector 12 which are held in place by a rigid housing 54 within the light-tight case 58. The rigid housing 54 prevents undesired movement of the components after assembly and calibration during manufacture. This facilitates a repeatable accurate alignment of the assay cartridge 52. Additionally, the light-tight case 58 comprises feet 56 which add stability and prevent the apparatus from moving which may lead to misalignment. The feet 56 are made of rubber. In other examples, not illustrated herein, the feet may be made from any other material capable of providing the required stability and surface compliance.

FIG. 9C shows the light-tight case 58 with the outer enclosure 60 having been moved vertically into an "open" position. The movement of the outer enclosure 60 to an "open" position enables the insertion of an assay cartridge 52. The outer enclosure 60 can be spring loaded and moved manually into an "open" or "closed" position by the user, or the vertical movement can be automated. A sensor (not shown) can be configured to indicate that the outer enclosure 60 is in the "closed" and/or "open" position.

Figure 9D:
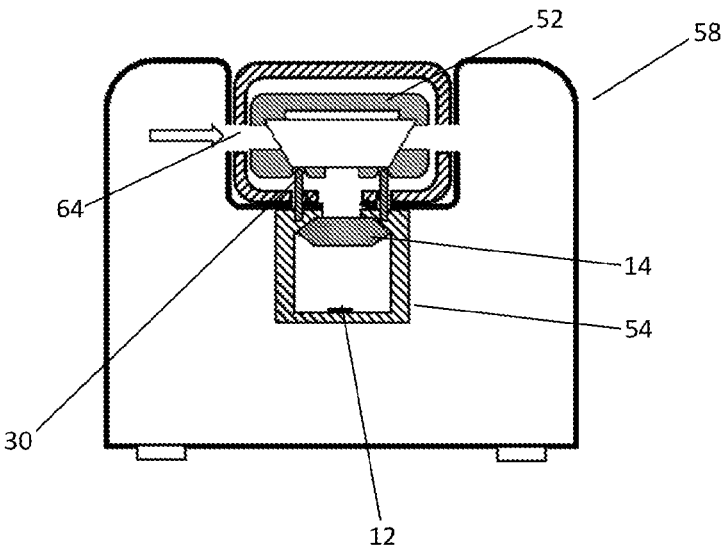
FIG. 9D shows the light-tight case in a closed position with an assay cartridge inserted.

FIG. 9D shows the light-tight case 58 with the outer enclosure 60 in a "closed" position with an assay cartridge 52 inserted into the outer enclosure 60. The closing of the outer enclosure 60 moves the assay cartridge 52 in the z-dimension and along the focal plane. The weight of the assay cartridge 52 aligned with a gravitation field, accurately positions the assay cartridge 52 facilitated by the location pins 30 and the chamfers/angles of the base of the cartridge. Additionally or alternatively a bias plate (not shown) can be used to facilitate the alignment. The accurate alignment of the assay cartridge 52 ensures an incident light beam can pass through an aperture 64 in the outer enclosure 60 and reach the assay cartridge 52 where an evanescent excitation field is generated, in use, via Total Internal Reflection.

In addition to facilitating an accurate alignment in the z-dimension, the outer enclosure 60 also acts as a lid for the assay cartridge 52 and prevents the user from being able to access the assay cartridge 52 whilst the apparatus is in use. This prevents the user being exposed to the excitation light source. In addition, the outer enclosure 60 protects the internal components of the apparatus from the environment which facilitates cleanliness of the device. Maintaining device cleanliness is important for a repeatable accurate alignment of assay cartridges 52. Alternatively, or additionally, the imaging lens 14 may comprise a flap or iris (not shown) which protects the imaging lens 14 whilst the outer enclosure 60 is in the "open" position.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

It will further be appreciated by those skilled in the art that although the invention has been described by way of example with reference to several embodiments. It is not limited to the disclosed embodiments and that alternative embodiments could be constructed without departing from the scope of the invention as defined in the appended claims.

The invention claimed is:

1. An apparatus for detecting the presence and/or the quantity of a target component in a sample, the apparatus comprising an integrated assay, the assay cartridge comprising a detection reagent and a capture component at a location in the assay cartridge, the apparatus comprising:

a detector for detecting the amount of light scattered, transmitted or emitted by the detection reagent to provide an indication of the presence and/or the quantity of the target component within the sample;

a lens configured to focus the light onto the detector;

an excitation light source configured to generate a light beam; and a plurality of location pins rigidly held in position relative to the lens and detector defining a location of the assay cartridge along the optical path from the location of the capture component to the detector at which the assay cartridge is located in use, wherein the plurality of location pins, rigidly held in position, are further configured such that the capture component location, in use, is focused on the detector via the lens.

2. The apparatus according to claim 1, wherein each of the three location pins are positioned away from the optical path of the detector.

3. The apparatus according to claim 1, further comprising a location plate on which the location pins are positioned.

4. The apparatus according to claim 1, wherein each location pin has a distal end on which to locate the cartridge, the distal ends of the pins having a curved tip.

5. The apparatus according to claim 4, wherein the location pins are stainless and corrosion protected.

6. The apparatus according to claim 1, further comprising a biasing element configured to bias the assay cartridge onto the location positions.

7. The apparatus according to claim 6, wherein the biasing element configured to bias the assay cartridge onto the location pins comprises at least one of: a mechanical biasing element; an electromagnetic biasing element; a magnetic biasing element; a pneumatic biasing element; a hydraulic biasing element; an inflatable pad; a heat actuated material; or a piezoelectric element.

8. The apparatus according to claim 1, wherein the assay cartridge is loaded onto the location pins along the optical path.

9. The apparatus according to claim 1, further comprising an indicator configured to detect the presence of, and identification, of a cartridge.

10. The apparatus according to claim 9, wherein the indicator comprises an electrical connection with the cartridge.

11. The apparatus according to claim 9, wherein the indicator uses RFID.

12. The apparatus according to claim 1, further comprising a reference checker to detect and check the location of one or more reference spots in the cartridge.

13. The apparatus according to claim 12, wherein the reference checker determines the focus of one or more reference spots.

14. The apparatus according to claim 12, wherein the reference checker compares the location of the one or more reference spots to a stored location to determine alignment accuracy.

15. The apparatus according to claim 1, wherein the target component is a specific peptide or protein or nucleic acid or small molecule.

16. The apparatus according to claim 1, wherein the sample is a saliva sample.

17. An apparatus according to claim 1, wherein the sample forms part of a free flow assay.

\* \* \* \* \*